United States Patent [19]

Mijers et al.

[11] Patent Number: 4,624,660
[45] Date of Patent: Nov. 25, 1986

[54] AUTOMATIC INJECTION DEVICE

[75] Inventors: Jan W. M. Mijers; Gillis P. van der Wal, both of Olst, Netherlands

[73] Assignee: Duphar International Research B.V., Weesp, Netherlands

[21] Appl. No.: 782,697

[22] Filed: Oct. 1, 1985

[30] Foreign Application Priority Data

Nov. 2, 1984 [NL] Netherlands .......................... 8403326

[51] Int. Cl.⁴ .............................................. A61M 5/20
[52] U.S. Cl. .................................................. 604/136
[58] Field of Search ................ 604/135, 136, 137, 232, 604/187, 131

[56] References Cited

U.S. PATENT DOCUMENTS

| | | | |
|---|---|---|---|
| 3,712,301 | 1/1973 | Sarnoff ................................. | 604/136 |
| 3,882,863 | 5/1975 | Sarnoff et al. ...................... | 604/136 |
| 4,031,893 | 6/1977 | Kaplan et al. ...................... | 604/136 |
| 4,226,235 | 10/1980 | Sarnoff et al. ...................... | 604/136 |

*Primary Examiner*—John D. Yasko
*Attorney, Agent, or Firm*—Stevens, Davis, Miller & Mosher

[57] ABSTRACT

The invention relates to an automatic injection device comprising an assembly of a discharge mechanism, a cartridge holder of synthetic material and a cartridge which is slidably accommodated in the cartridge holder. The cartridge includes a glass ampoule, if desired, enveloped by a sheath of shrinkable sheet, the ampoule consisting of an ampoule cylinder in which an injection liquid or various injection liquids separated from each other by stoppers and a piston which can be moved in the ampoule cylinder are provided. The assembly also includes a connection means for an injection needle in which or to which the injection needle, if desired, covered by a guard to maintain the needle in a sterile condition, is connected, and a shoulder between the ampoule cylinder and the needle connection means. The cartridge holder consists of a sleeve-like rear portion which is open at each end and which, after actuating the injection device, is traversed by the ampoule cylinder and the inner surface of which has substantially the same transverse dimensions over the whole length, and a front portion which forms one assembly with the sleeve-like portion and, after actuating the syringe, serves to discontinue the forward movement of the cartridge in the holder and to allow passage of the needle. The sleeve-like portion of the cartridge holder has a five-sided to fourteen-sided cross-section over a length which is at least equal to the length of the ampoule cylinder and is proportioned such that the ampoule cylinder engages the inner side surfaces of the sleeve-like portion with friction. The invention furthermore relates to a cartridge holder for the injection device.

6 Claims, 6 Drawing Figures

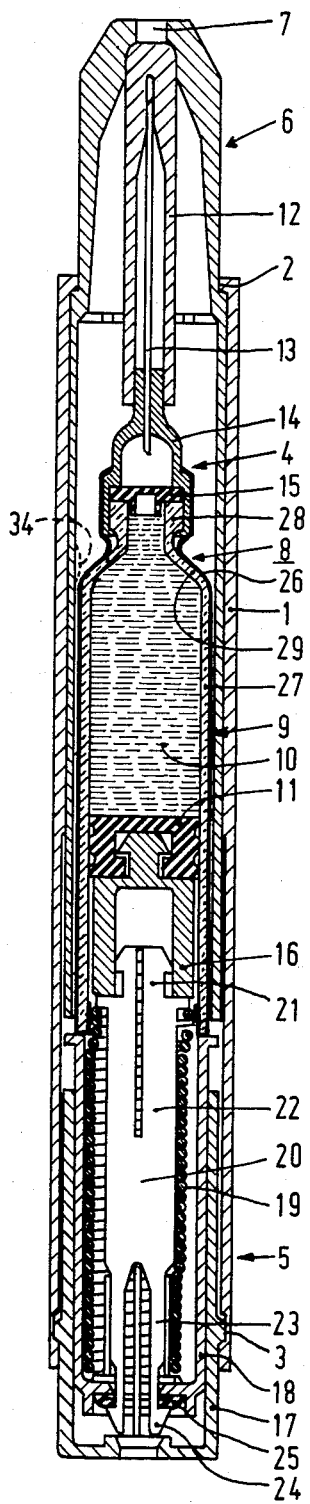
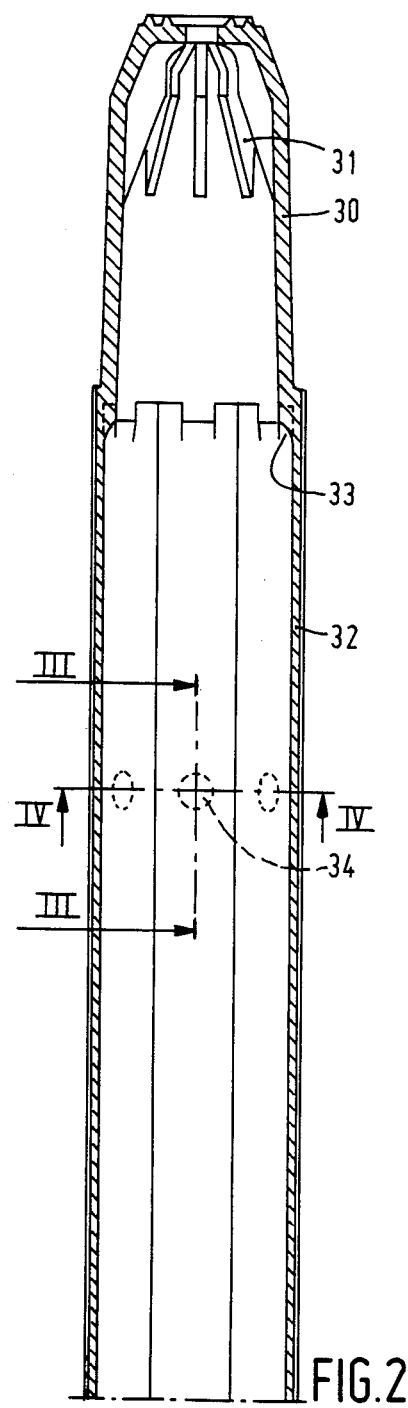

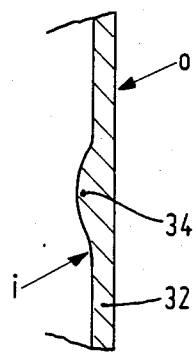
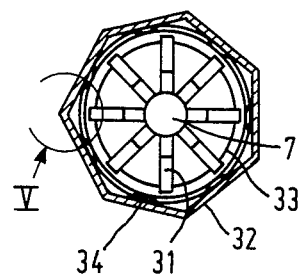
FIG. 3         FIG. 4
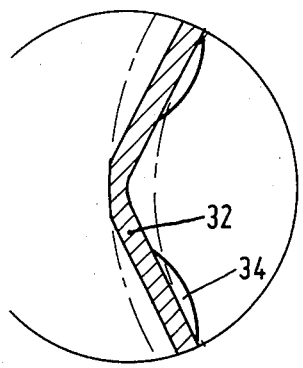
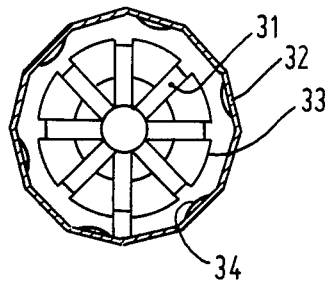
FIG. 5         FIG. 6

AUTOMATIC INJECTION DEVICE

The invention relates to an automatic injection device comprising an assembly of a discharge mechanism, a cartridge holder of a synthetic material and a cartridge which is slidably accomodated in the cartridge holder. The cartridge comprises a glass ampoule, which consists of an ampoule cylinder containing an injection liquid or various injection liquids separated from each other by stoppers and a piston which can be moved in the ampoule cylinder. The assembly further includes a connection means for an injection needle in which or to which the injection needle is connected, and a shoulder between the ampoule cylinder and the needle connection means. The cartridge holder consists of a sleeve-like rear portion, which is open at each end and which, after actuating the injection device, is traversed by the ampoule cylinder and the inner surface of which has substantially the same transverse dimensions over the whole length, and a front portion which forms one assembly with the sleeve-like portion and, after actuating the syringe, serves to discontinue the forward movement of the cartridge in the holder and to allow passage of the needle.

Such an injection device, namely for one injection liquid, is known from British Patent Specification No. 1,528,735. The device disclosed in said Patent Specification moreover comprises a spacer element with which the contents of the ampoule can be reduced at will, and a needle guard of a flexible material which keeps the needle sterile during storage of the device. Such a needle guard is an excellent provision and is preferably used also in the syringe according to the present invention.

An injector related to the injection device known from the above British Patent Specitication is described in U.S. Pat. No. 3,712,301. In the species shown in FIGS. 4 to 6 of this latter patent specification the cartridge holder is internally provided with three longitudinally extending ribs to distort the resilient sealing end portion of the ampoule during operation of the injector, thereby providing openings for flow of air in said end portion, and thus allowing the air locked in between the front of the cartridge holder and the front of the ampoule to escape backwards.

An automatic injection device as mentioned in the opening paragraph in which various injection liquids separated from each other by stoppers are accommodated is disclosed in European Patent Application No. 72057 in the name of the Applicants.

It has been found that when the injector known from the above British Patent Specification No. 1,528,735 or U.S. Pat. No. 3,712,301 is used, fracture of the glass ampoule often occurs, in particular when the ampoule is manufactured from unhardened glass. Upon actuating the device, apparently the material of the ampoule often cannot withstand the forces occuring upon relaxation of the spring forming part of the discharge mechanism. This disadvantage can be checked by using an ampoule around which a sheath of shrinkable plastic sheet has been shrunk, as described recently in European Patent Application No. 107874 also in the name of the Applicants. The injection device according to the present invention preferably comprises a glass ampoule enveloped by a sheath of shrinkable sheet.

Automatic injection devices have been developed in particular for use by persons who have to administer an injection into their own body at a given instant which is not known beforehand. These persons include, for example, soldiers after having been exposed to a battle gas of the enemy, for example, a nerve gas. It should therefore be obvious that stringent requirements have to be imposed upon automatic injectors as regards their reliability. Such devices are usually stored for many years at a time and in addition are carried with the potential user for long periods of time under varying conditions. Despite these facts the reliability of the injector must remain sufficiently ensured at the critical instant when the injection is required. In fact, at said critical instant the user's life may depend on the ready operation of the injection device.

Automatic injection devices are exposed to heavy shocks in particular when used by soldiers in the field. In order that in these circumstances the devices remain intact, i.e. still operate at the critical moment, high requirements must also be imposed upon the shock resistance of the injectors. It is therefore required, in particular by military authorities in various countries, that even extreme droptests do not adversely influence the ready operation of automatic injection devices. An example of a very extreme droptest is a test in which the automatic injector, without any further external protection means, falls from a height of 1.50 m on a granite table. It has been found that thereafter approximately 15% of the automatic injectors no longer operated well even when the glass ampoule thereof was enveloped by a sheath of shrinkable sheet.

It is the object of the present invention to provide an automatic injection device which maintains its ready operation also under the above-described extreme conditions.

This object can be achieved by means of an automatic injection device of the type mentioned in the opening paragraph which, according to the invention, comprises a cartridge holder the sleeve-like portion of which, over a length which is at least equal to the length of the ampoule cylinder, has a five-sided to fourteen-sided cross-section and is proportioned such that the ampoule cylinder has a frictional engagement with the inner side surfaces of said sleeve-like portion.

It has surprisingly been found that when such a cartridge holder is used, not only the shock resistance of the automatic injection device is improved such that an ampoule of unhardened glass may be used without any objection, but also that the subtle cooperation between the cartridge holder and ampoule is not adversely influenced. On the contrary, it has been found that upon actuating the injector according to the invention, the ampoule cylinder can move forward even smoother and better centred in the cartridge holder sleeve thus formed, while nevertheless the air in front of the ampoule can flow away backwards without any hindrance between the outer wall of the glass ampoule and the inner wall of the cartridge holder sleeve. Moreover, upon assembling the injection device according to the invention, positioning the cartridge in the cartridge holder is not hampered because of the flexibility of the plastic wall of the cartridge holder sleeve. The cartridge holder can be manufactured in a simple manner and hence cheaply, for example, by injection moulding, from a form-retaining slightly resilient synthetic material, for example, from polypropylene.

It has furthermore been found in addition that the rigidity of the cartridge holder of the injection device according to the invention is greater than that of a known cartridge holder, as described, for example, in the above-mentioned British Patent Specification No. 1,528,735; of course, this applies to equal wall thicknesses of the cartridge holders. As a result of this, the bending resistance of the injection device is increased so that an extra contribution is provided to the reliability of the device. When used under extreme conditions, for example by soldiers in the field, the automatic injector may also be subjected to a large bending load, as a result of which the risk of fracture of the glass ampoule increases. Improvement of the bending resistance of the injection device hence is of great importance.

It has been found that the advantages of the syringe according to the invention appear in particular when the sleeve-like part of the cartridge holder has a six-sided to twelve-sided cross-section. A cartridge holder sleeve having a seven-sided cross-section has proved to be extremely suitable.

Without extra provisions on the inside of the cartridge holder sleeve, the possibility is not excluded that, when the injection device falls down on its front side or nose, the cartridge may slightly move forward in the cartridge holder sleeve. It may then occur that the needle emanates from the cartridge holder as a result of which the sterility of the needle is lost and, which is more serious, the tip of the needle is damaged. It has now been found that this risk can be avoided by providing at least three inner side surfaces of the sleeve-like portion of the cartridge holder of the injection device according to the invention with radially positioned raised portions which are distributed over the circumference of the sleeve-like portion and form one assembly therewith. During storage of the syringe these raised portions engage the ampoule shoulder or are positioned at a short distance in front of it. This provision which provides an extra contribution to the reliability of the injection device may be considered as a particular aspect of the invention because it can be used successfully only in a cartridge holder for an injection device according to the invention, i.e. a cartridge holder having a five-sided to fourteen-sided sleeve-like rear portion. As a matter of fact, the flat side walls in such a cartridge holder sleeve are so resilient that the raised portions thereon, provided their dimensions are suitable, can easily by pushed aside by the ampoule cylinder upon actuation of the syringe, so that the forward movement of the cartridge in the holder is not prevented or impeded in such manner that the injector no longer operates normally. On the other hand, the raised portions on the inner side surfaces of the cartridge holder sleeve are sufficient to prevent inadvertent movement of the ampoule within the holder, so to keep the cartridge in the cartridge holder in its place when the injector falls on its nose. Often all the inner side surfaces of the sleeve-like portion of the cartridge holder are provided with raised portions so that a seven-sided cartridge holder sleeve also comprises seven raised portions, but for the intended purpose fewer raised portions will suffice.

The above provisions to improve the shock resistance of an automatic injection device are intended in particular for an automatic injector the ampoule of which is manufactured from unhardened glass. If the glass has been subjected to a special hardening, the risk of fracture upon falling or impacting of the injector generally is comparatively small. However, as stated in the European Patent Application No. 107874 mentioned hereinbefore such a hardening process is comparatively expensive and hence less attractive for automatic injectors which are manufactured in large quantities.

The invention furthermore relates to a cartridge holder for the injection device described hereinbefore the sleeve-like portion of which has a five-sided to fourteen-sided cross-section over the whole or at least a part of its length.

The invention will now be described in greater detail with reference to preferred embodiments which are shown in the drawings, in which:

FIG. 1 is a longitudinal sectional view of an injector according to the invention;

FIG. 2 is a longitudinal sectional view of a cartridge holder as show in FIG. 1 but this time on a slightly larger scale;

FIG. 3 is an enlargement of a detail of a longitudinal sectional view of the wall of the FIG. 2 cartridge holder taken on the line III—III of FIG. 2;

FIG. 4 is a cross-sectional view of the cartridge holder shown in FIG. 2 taken on the line IV—IV in FIG. 2, viewed in the direction of the nose portion of the holder;

FIG. 5 is an enlargment of a detail of the part of the cross-sectional view of FIG. 4 indicated by V; and FIG. 6 is a cross-section view comparable to that of FIG. 4 but of a different embodiment of the cartridge holder.

The injector shown in FIG. 1 is in broad outline equal to that described and shown in the above-mentioned European Patent Application No. 107874. The embodiment shown in FIG. 1 is only one example of an automatic injection device in which the provisions for improving the shock resistance can be advantageously used. Other suitable examples of such injection devices are described and shown in European Patent Application No. 72057.

The injector shown in FIG. 1 comprises an outer sleeve 1 having an inwardly bent edge 2 and circumferential groove 3, in which a cartridge assembly 4 and a discharge mechanism 5 are accommodated. The cartridge assembly comprises a cartridge holder 6 which fits in the outer sleeve and at its front end has a circular aperture 7, and a cartridge 8 which is movable in the cartridge holder. The cartridge comprises an ampoule 9 consisting of an ampoule cylinder 27, a neck 28, and a shoulder 29 between cylinder and neck. An injection needle 13 comprising a rubber needle guard 12 is connected on the neck of the ampoule by means of a needle holder 14. An injection liquid 10 is present in the ampoule between a piston 11 movable in the ampoule cylinder and a membrane 15 provided between the neck of the ampoule and the needle holder. Said membrane keeps the injection liquid separated from the needle during storage of the injector, but bursts open during use of the syringe so that the injection liquid can reach the needle cannula. Furthermore, a spacer element 16 is provided behind the piston with which the volume of the ampoule for the injection liquid is reduced.

As the injector described in British Patent Specification No. 1,528,735, the discharge mechanism comprises an outer gun sleeve 17 locked in groove 3 of outer sleeve 1 and an inner gun sleeve 18 slidably accomodated in the outer gun sleeve and comprising a coil spring 19 as a power source. The coil spring fits around a plunger 20 with a sufficient amount of play, the plunger consisting of a plunger head which is inserted in the spacer element, a central portion 12 and an end portion 23. The end portion consists of four resilient prongs the conical ends 24 of which bear on a metal sealing ring 25 around an aperture in the rear face of the inner gun sleeve. In the FIG. 1 syringe the safety member consisting of a cap with a safety pin which may extend between the prongs of the plunger, has already been removed so that the syringe is ready for use. A sheath 26 of PVC shrinkable sheet is shrunk around the whole ampoule, including its neck and rear edge.

For further explanation, FIG. 2 shows the cartridge holder 6 of FIG. 1 on an enlarged scale. The cartridge holder consists of a tapering nose portion 30 which on its front comprises longitudinal ribs 31 for centering the needle guard 12. A circular aperture 7 is recessed in the front face of nose portion 30. The nose portion adjoins a sleeve-like rear portion 32 having increased transverse dimensions which are equal or substantially equal over the whole length. The shoulder 33 formed between the nose portion and the sleeve-like portion forms an abutment for the ampoule shoulder 29 in the position in which the cartridge is maximally moved forwards in the cartridge holder. As is shown clearly in the cross-sectional view of FIG. 4, the sleeve-like rear portion of the cartridge holder has a seven-sided cross-section.

In the cross-sectional view of the cartridge holder shown in FIG. 4 and viewed in the direction of the nose portion, the shoulder 33 formed by the nose portion of reduced diameter, the centering ribs 31 and the aperture in the front face of the nose portion are also shown. Seven radially positioned raised portions 34 which form one assembly with the cartridge holder wall are provided on the inner side surfaces of the sleeve-like rear portion of the cartridge holder. As is shown in FIG. 1, said raised portions constitute an abutment for the ampoule shoulder 29; upon actuating the injector, however, the ampoule can easily be moved forwards, the raised portions positioned on the resilient side walls of the sleeve-like portion of the cartridge holder being pushed aside without any difficulty (overridden).

For further explanation, FIG. 5 shows on an enlarged scale a detail of a wall part of the cartridge holder sleeve with two raised portions. FIG. 3 furthermore shows on an enlarged scale a detail of a longitudinal sectional view of the cartridge holder wall taken on the line III—III of FIG. 2. In FIG. 3, i denotes an inner side surface and o denotes an outer side surface. FIG. 6 finally is a cross-sectional view which is comparable to that of FIG. 4, but this time through a cartridge holder having a twelve-sided rear portion. The reference numerals correspond to those of FIG. 4.

The use of the injection device according to the invention is the same as that of the one described in British Patent Specification No. 1,528,735 mentioned hereinbefore and needs no further explanation.

Injection devices according to the invention in which the ampoule had been manufactured from unhardened glass around which a sheath of shrinkable sheet had been shrunk according to the above-mentioned European Patent Application No. 107874 and which had been provided with a cartridge holder having a seven-sided sleeve portion as described hereinbefore, were compared with identical injectors comprising a cartridge holder having a cylindrical sleeve portion internally provided with three longitudinal ribs (as described in the above U.S. Pat. No. 3,712,301). The cartridge holders had been manufactured from polypropylene by injection moulding. The injectors to be tested were subjected to a droptest, either by dropping them flat on a granite table from a height of 1.50 meters (droptest A), or by dropping them six successive times from a height of 1.20 meters on a concrete floor (droptest B). The injectors were then "discharged". The following results were obtained:

| injector cartridge holder sleeve | glass ampoule | droptest | number of tested injectors | well expelled number | % |
|---|---|---|---|---|---|
| seven-sided | unhardened | A | 50 | 49 | 98 |
| seven-sided | " | B | 50 | 50 | 100 |
| cylindrical | " | A | 50 | 43 | 86 |

"Well expelled" is to be understood to mean that upon "discharge" of the injector, the injection liquid has left the injector through the injection needle and has not prematurely leaked away from the ampoule due to fracture thereof.

From the above results it appears that when a cartridge holder sleeve having a plurality of flat sides is used instead of a cylindrical one, the percentage of fracture of the ampoules in droptests of automatic injection devices can be reduced to an acceptable percentage.

We claim:

1. An automatic injection device comprising an assembly of a discharge mechanism, a cartridge holder of a synthetic material and a cartridge which is slidably accomodated in the cartridge holder, which cartridge comprises a glass ampoule, if desired enveloped by a sheath of shrinkable sheet, said ampoule consisting of an ampoule cylinder in which an injection liquid or various injection liquids separated from each other by stoppers and a piston which can be moved in the ampoule cylinder are provided, a connection means for an injection needle in which or to which the injection needle, if desired, covered by a guard to maintain the needle in a sterile condition, is connected, and a shoulder between ampoule cylinder and needle connection means, the cartridge holder consisting of a sleeve-like rear portion which is open at each end and which, after actuating the injection device, is traversed by the ampoule cylinder and the inner surface of which has substantially the same transverse dimensions over the whole length, and a front portion which forms one assembly with the sleeve-like portion and, after actuating the syringe, serves to discontinue the forward movement of the cartridge in the holder and to allow passage of the needle, characterized in that the sleeve-like portion of the cartridge holder has a five-sided to fourteen-sided cross-section over a length which is at least equal to the length of the ampoule cylinder and is proportioned such that the ampoule cylinder engages the inner side surfaces of said sleeve-like portion with friction.

2. An injection device as claimed in claim 1, characterized in that the sleeve-like portion of the cartridge holder has a six-sided to twelve-side, preferably a seven-sided, cross-section.

3. A injection device as claimed in claim 1 or 2, characterized in that at least three inner side surfaces of the sleeve-like portion of the cartridge holder comprise radially positioned raised portions distributed over the circumference of the sleeve-like portion and forming one assembly therewith, which raised portions, during storage of the syringe, engage the ampoule shoulder or are positioned at a short distance in front of it, but which portions have such dimensions that upon actuating the syringe they are pushed aside by the ampoule cylinder so that the forward movement of the cartridge in the holder is not hampered.

4. An injection device as claimed in any of the preceding claims, characterized in that the ampoule is manufactured from unhardened glass.

5. A cartridge holder for an injection device as claimed in any of the preceding claims, consisting of a sleeve-like rear portion which is open at each end and the inner surface of which has substantially the same transverse dimensions over the whole length, and a front portion which forms one assembly with the sleeve-like portion and which comprises means to discontinue the forward movement of the cartridge in the holder after actuating the syringe and to allow passage of the needle, characterized in that the sleeve-like portion has a five-sided to fourteen-sided cross-section over the whole or at least a part of the length.

6. A cartridge holder as claimed in claim 5, characterized in that at least three inner side surfaces of the sleeve-like portion thereof comprise radially positioned raised portions distributed over the circumference of the sleeve-like portion and forming one assembly therewith.

* * * * *